US010346968B2

(12) United States Patent
Yau et al.

(10) Patent No.: US 10,346,968 B2
(45) Date of Patent: Jul. 9, 2019

(54) MACHINE CONDITION MONITORING SYSTEM USING THREE DIMENSIONAL THERMOGRAPHY

(71) Applicants: Kwok Keung Yau, New Territories (HK); Sze Chai Yau, New Territories (HK)

(72) Inventors: Kwok Keung Yau, New Territories (HK); Sze Chai Yau, New Territories (HK)

(*) Notice: Subject to any disclaimer, the term of this patent is extended or adjusted under 35 U.S.C. 154(b) by 203 days.

(21) Appl. No.: 15/618,101

(22) Filed: Jun. 8, 2017

(65) Prior Publication Data

US 2017/0372468 A1    Dec. 28, 2017

(30) Foreign Application Priority Data

Jun. 24, 2016   (CN) .......................... 2016 1 0467367

(51) Int. Cl.
| | | |
|---|---|---|
| *G01J 5/00* | (2006.01) | |
| *G06T 7/00* | (2017.01) | |
| *H04N 13/218* | (2018.01) | |
| *G02B 5/10* | (2006.01) | |
| *H04N 5/232* | (2006.01) | |

(Continued)

(52) U.S. Cl.
CPC ........... *G06T 7/0004* (2013.01); *G01N 25/72* (2013.01); *G02B 5/10* (2013.01); *H04N 5/23296* (2013.01); *H04N 5/33* (2013.01); *H04N 13/218* (2018.05); *G06T 2207/10021* (2013.01); *G06T 2207/10028* (2013.01); *G06T 2207/10048* (2013.01); *G06T 2207/30164* (2013.01)

(58) Field of Classification Search
CPC ................ G01J 5/08; G01J 2005/0077; G01J 2005/0081; G01J 1/0266; G01J 5/00; G01J 5/0066; G06F 3/0304; G01N 25/72; G01N 21/35; G01N 21/359; G01N 2201/0636
USPC ......................................................... 702/136
See application file for complete search history.

(56) References Cited

U.S. PATENT DOCUMENTS 3,988,726 A * 10/1976 Reiss ..................... G08B 13/19
340/567
4,271,359 A    6/1981 Herwig et al.
(Continued)

FOREIGN PATENT DOCUMENTS

CN    102967373 A    3/2013
CN    203141834 U  *  8/2013
(Continued)

OTHER PUBLICATIONS

2013 IEEE International Conference on Robotics and Automation (ICRA); May 1, 2013, Stephen Vidas et al., pp. 2311-2318.

*Primary Examiner* — Gail Kaplan Verbitsky
(74) *Attorney, Agent, or Firm* — George G. Wang; Bei & Ocean

(57) ABSTRACT

The present disclosure discloses a machine condition monitoring system using three-dimensional thermography, which may automatically alert an operation when detecting any anomalies in three-dimensional thermal imaging of a machine. The machine condition monitoring system is for monitoring conditions of a machine and recording three-dimensional thermal imaging of the machine, comprising: a pan-tilt-zoom thermal imaging camera, at least one infrared reflective convex mirror, and a computer server.

8 Claims, 3 Drawing Sheets

(51) Int. Cl.
*H04N 5/33* (2006.01)
*G01N 25/72* (2006.01)

(56) References Cited

U.S. PATENT DOCUMENTS

| | | | | |
|---|---|---|---|---|
| 4,975,581 A | * | 12/1990 | Robinson | A61B 5/14532 |
| | | | | 250/339.09 |
| 5,521,376 A | * | 5/1996 | Mileski | G01S 7/4813 |
| | | | | 250/239 |
| 6,439,764 B1 | | 8/2002 | Engering et al. | |
| 2003/0214640 A1 | * | 11/2003 | Kimura | H04N 5/74 |
| | | | | 353/122 |
| 2016/0006951 A1 | * | 1/2016 | Moghadam | G03B 35/02 |
| | | | | 348/164 |
| 2017/0132467 A1 | * | 5/2017 | Trinh | G06T 7/70 |
| 2018/0031491 A1 | * | 2/2018 | Thompson | G01N 21/94 |
| 2019/0032507 A1 | * | 1/2019 | Bewlay | F01D 21/003 |

FOREIGN PATENT DOCUMENTS

| | | | |
|---|---|---|---|
| CN | 204027583 U | * | 12/2014 |
| CN | 204255506 U | | 4/2015 |
| CN | 105203210 A | | 12/2015 |
| WO | WO03/038403 A | | 5/2003 |
| WO | WO2014/003433 A1 | | 1/2014 |
| WO | WO2015155354 A1 | | 10/2015 |

\* cited by examiner

MACHINE CONDITION MONITORING SYSTEM USING THREE DIMENSIONAL THERMOGRAPHY

FIELD OF THE INVENTION

The present disclosure relates to a technology for diagnosing a condition of a machine, particularly to diagnosing an anomaly of the machine evident by thermal changes in different parts of the machine; more specifically, the present disclosure relates to a machine condition monitoring system using three-dimensional thermography, which system may automatically alert an operator when detecting any anomaly in three-dimensional thermal imaging of the machine.

BACKGROUND OF THE INVENTION

Nowadays, thermographic cameras/thermal imagers are becoming more rugged, user-friendly, and affordable. Thus, infrared thermal imaging/infrared thermography has been widely exploited in various industrial applications, particularly in fault detection and predictive maintenance. Not only instant thermal imaging of equipment may be inspected to identify any unexpected hot spots or cold spots, but also potential component failures may be instantly identified, thereby minimizing associated losses in downtime, power outage, fires and catastrophic failures. In addition, the thermography has been applied more and more intensively for monitoring various types of electrical/electronic equipment, e.g., transformers, capacitor banks, overhead power lines, power supplies, substations, switchgears, and etc. The infrared thermography is becoming one of the most effective technologies for diagnosing conditions of a machine, which allows instant detection of anomalies with precise, non-invasive temperature measurement.

Here, FIG. 4 will be referenced to briefly introduce the working principle of an infrared thermal imager as prior art. Infrared thermography is a science of detecting and measuring radiation with a photoelectric device and establishing an interrelation between radiation and surface temperature. Radiation refers to transfer of heat occurring when radiation energy (electromagnetic wave) moves without a direct conductive medium. The working principle of a modern infrared thermal imager is detecting and measuring radiation with a photoelectric device and establishing an interrelation between radiation and surface temperature. All objects with a temperature above the absolute zero (−273° C.) will emit infrared radiation. With an infrared detector and an optical imaging object lens, the infrared thermal imager accepts the infrared radiation energy of a measured object, a distribution pattern of which infrared radiation energy is reflected onto a photosensitive element of the infrared detector, thereby obtaining an infrared thermogram corresponding to a heat distribution field on the surface of the object. Generally speaking, the infrared thermal imager transforms invisible infrared energy emitted by the object to a visible thermal image. Different colors on the thermal image represent different temperatures of the measured object. By checking the thermal image, the overall temperature distribution condition of the measured object may be observed, and heating of the measured object may be studied for determining subsequent work.

However, due to limitations of the state of the art, even in a very small electrical equipment room, a plurality of thermal imaging cameras are needed for monitoring machine conditions. Particularly for an oil filled transformer, thermal imaging of high- and low-voltage external bushing connections, cooling tubes, and cooling fans and pumps, as well as the surface of the transformer should be obtained to monitor any specific type of fault that may occur within the transformer. In this case, a plurality of thermal imaging cameras are needed to monitor different parts of the machine from different angles.

However, when the measured machine is in a compact environment, there is usually no extra space for installing thermal imaging cameras for monitoring the rear of the machine. In addition, a handheld thermal imager may also be used for thermal imaging of different parts of equipment in a compact environment. However, manpower is required to use the handheld thermal imager; besides, some parts of the machine are possibly inaccessible for thermal imaging. Further, a thermal image is usually obtained in a two-dimensional manner, which makes it very difficult to identify positions of anomalies of the machine.

SUMMARY OF THE INVENTION

To solve the technical problems above, an objective of the present disclosure is to monitor a condition of a machine such as a distribution transformer and locate a thermal anomaly safely and precisely in a three-dimensional model (3D model) manner. A machine condition monitoring system using thermography according to the present disclosure may automatically alert an operator when detecting any anomaly in three-dimensional thermal imaging of a machine.

A technical solution of the present disclosure provides a system for monitoring a working condition of a machine and recording three-dimensional thermal imaging of the machine, comprising: a pan-tilt-zoom thermal imaging camera, at least one infrared reflective convex mirror, and a computer server.

Preferably, in the system according to the technical solution, the infrared reflective convex mirrors are installed at strategic positions surrounding the monitored machine so as to reflect infrared rays emitted from different parts of the machine, and the pan-tilt-zoom thermal imaging camera captures reflected infrared rays from the convex mirrors at different preset positions.

Preferably, in the system according to the technical solution, thermal images captured by the pan-tilt-zoom thermal imaging camera are transmitted to the computer server for image processing and recording.

Preferably, in the system according to the technical solution, the computer server computes and configures the transmitted thermal images according to a plurality of physical characteristics so as to obtain actual infrared energies emitted from the machine.

Preferably, in the system according to the technical solution, the physical characteristics include a focal length of the convex mirror, a distance between the convex mirror and the monitored machine, and a distance and angle between the pan-tilt-zoom thermal imaging camera and the convex mirror.

Preferably, in the system according to the technical solution, the computer server maps, by computing and configuring, the thermal images from different parts of the monitored machine to a three-dimensional model of the machine, to obtain three-dimensional thermal imaging of the machine for further inspection.

Preferably, in the system according to the technical solution, the computer server compares temperatures at the different parts of the monitored machine with a predefined threshold and alerts an operator for notification if the three-dimensional thermal imaging has any unexpected hot spots or cold spots.

Preferably, in the system according to the technical solution, the computer server records changes of the three-dimensional thermal imaging over time, such that an operator may inspect an anomaly pattern over time to identify a fault type in the monitored machine.

The technical solution of the present disclosure is capable of monitoring all parts (including those non-line-at-sight parts) with a minimal number of thermal imaging cameras. In addition, with thermal images from different parts of the machine, three-dimensional thermal imaging may be produced so as to promptly and accurately locate any machine anomalies. The technical solution of the present disclosure may reduce investment on thermal inspection by exploitation of light reflection and refraction and guarantee that even those blocked non-line-at-sight parts may also be monitored with a minimal number of thermal imaging cameras. With a 3D model such as a Building Information Model (BIM), thermal anomalies may be visualized and accurately located.

The features, technical effects, and other advantages of the present disclosure will become apparent from the following description in conjunction with the accompanying drawings.

BRIEF DESCRIPTION OF THE ACCOMPANYING DRAWINGS

Now, the present disclosure will be described exemplarily with reference to the accompanying drawings, among which:

DETAILED DESCRIPTION OF THE PREFERRED EMBODIMENTS

Figure 1:
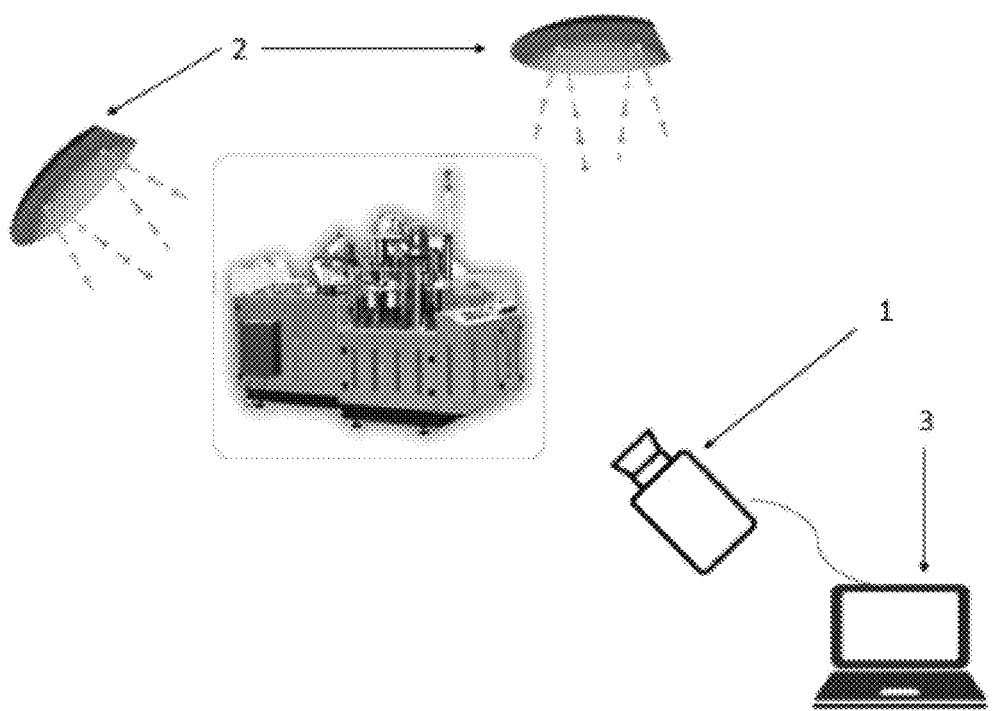
FIG. 1 is a structural diagram of a machine condition monitoring system using three-dimensional thermography according to an embodiment of the present disclosure.

Hereinafter, exemplary embodiments of the present disclosure will be described in detail with reference to the accompanying drawings, wherein like numbers in the description with reference to the accompanying drawings will be understood as referring to the same parts, components and structures; meanwhile, repetitive depictions will be avoided as much as possible. In this aspect, the embodiments as described herein may have different forms in different situations and should not be interpreted as limiting the depictions herein. Therefore, hereinafter, only embodiments are described with reference to the drawings to explain various aspects of the description. In the depictions infra, when well-known functions included herein and detailed depictions of configurations will possibly obscure the subject matter of the present disclosure, detailed depictions thereof will be omitted.

The terms used here are only used for illustrating, rather than limiting exemplary embodiments. A singular form used here is also intended to include a plural form, unless otherwise indicated in the context. It should also be understood that when terms "comprise" and/or "include" are used herein, they indicate existence of the described features, steps, operations, complements, elements and/or a combination thereof, but do not exclude existence or addition of one or more other features, steps, operations, components, elements and/or a combination thereof.

Exemplary embodiments may be described with functional block units and various processing steps. Such functional blocks may be implemented by any number of hardware, software, and/or firmware units configured to perform specific functions. For example, exemplary embodiments may adopt various kinds of integrated circuit units performing various functions in one or more microprocessors or under control of other control devices, e.g., memory elements, processing elements, logical elements and lookup tables, etc. Similarly, when the elements in the exemplary embodiments are implemented using software programming or software units, the present disclosure may be implemented with any programming or script language (e.g., C, C++, Java, assembly, etc.) using algorithms executed by any combination of data structure, object, process, routing or other program elements. The functional aspects may be implemented by an algorithm executed at one or more processors. In addition, the present disclosure may adopt traditional technologies for electronic structures, signal processing and/or control, data processing, and etc. The terms (e.g., "mechanism," "element," "means," "units," and etc.) may be used broadly, not limited to mechanical and physical components. The terms may contain a meaning of a series of software routines connected to a processor or the like.

Hereinafter, FIGS. 1-3 will be referenced to elaborate the technical contents and configuration features of the preferred embodiments of the present disclosure, as well as the technical objectives and technical effects as achieved.

FIG. 1 is a structural diagram of a machine condition monitoring system using three-dimensional thermography according to an embodiment of the present disclosure. As illustrated in FIG. 1, a machine condition monitoring system according to the present disclosure comprises a pan-tilt-zoom thermal imaging camera 1, two infrared reflective convex mirrors 2, and a computer server 3. Needless to say, in actual applications, the number of infrared reflective convex mirrors 2 is not limited to two, which may be increased or decreased according to field conditions of the machine and specific application scenarios. The infrared reflective convex mirrors 2 are for reflecting the infrared ray emitted by the machine to the pan-tilt-zoom thermal imaging camera 1. Because the infrared ray emitted by the machine advances in a straight line, a plurality of infrared reflective convex mirrors 2 may be installed at different positions of the equipment room according to needs, so as to reflect the infrared ray emitted by the machine from a plurality of strategic angles.

As is well known, a general convex mirror (also referred to a wide-angle mirror, a reflector, or a turning mirror) is mainly applied for expanding a driver's field of view at various kinds of bends and corners so as to find an opposite vehicle at a bend, thereby reducing traffic accidents; and it is also applied for preventing burglary in supermarkets and monitoring dead angles. Those skilled in the art can easily understand that the infrared reflective convex mirror diverges infrared ray; with this principle, the present disclosure may expand the system's monitoring field of view. In other words, just because the size of reflected images from the infrared reflective convex mirrors is relatively small, even in a narrow visual angle due to a narrow equipment room environment, thermal images of more parts of the monitored machine may still be obtained. This is crucial for application in a compact environment, because it usually has no extra space for installing a thermal imaging camera for monitoring the rear of a machine.

In addition, infrared rays coming from different parts of the machine are reflected to the pan-tilt-zoom (PTZ) thermal imaging camera 1 through the convex mirrors 2. The PTZ thermal imaging camera 1 captures the reflected infrared rays from different convex mirrors 2 at different preset positions, such that three-dimensional thermal imaging of the whole machine may be created using a single PTZ thermal imaging camera 1. Here, it needs to be noted that PTZ is abbreviated for pan-tilt-zoom (concepts for security monitoring facilities), representing all-round (left, right/up, down) movement of the gimbal, magnification-change of lens, and zooming control. Distinct from common surveillance cameras, the lens of the PTZ camera may have different functions: left-right panning, up-down tilting, and zooming. The PTZ camera may change the angle, coverage, and definiteness of photographing at any time, such that a better surveillance effect may be achieved compared with conventional cameras that can only make a single movement. Each preset position corresponds to a respective position programmed for panning, tilting, and zooming a joystick. The preset positions are stored at the PTZ camera end or video management system side.

According to well-known optical theories, images reflected from a plurality of infrared reflective convex mirrors 2 are smaller than the actual objects, while images from the convex mirrors will be distorted; therefore, computation and configuration should be performed in the computer server 3 according to some physical characteristics (e.g., focal length of the convex mirror, distance between the convex mirror and the monitored machine, and the actual distance and angle between the PTZ thermal imaging camera 1 and the infrared reflective convex mirror 2, etc.), so as to obtain true values of infrared energies emitted from different parts of the monitored machine, i.e., actual infrared energies from different parts of the monitored machine.

The computer server 3 further maps thermal images from different parts of the monitored machine to a 3D model of the monitored machine, resultant three-dimensional thermal imaging of the machine being available for further inspection. In other words, through computation by the computer server 3, actual infrared energies from different parts of the monitored machine are mapped to the 3D model of the monitored machine. In the computer server 3, for example, temperatures from different parts of the monitored machine are compared with a predefined threshold. If any unexpected hot spots or cold spots exist in the three-dimensional thermal imaging, an alert will be sent to the operator for notification. Besides, the computer 3 also records change of the three-dimensional thermal imaging over time; in this way, an anomaly pattern over time may be inspected to facilitate identification of a fault type in the machine.

In view of the above, different from the prior technical solution using an infrared imager, the present disclosure obtains the actual infrared energies from different parts of the monitored machine by reflecting the rear (non-line-at-sight parts) of the monitored machine using infrared reflective convex mirrors 2 and by computing with the computer server 3 to perform relevant processing to the images distorted due to reflection. Additionally, for the front (line-at-sight parts) of the monitored machine that can be directly monitored by the PTZ thermal imaging camera 1, its actual thermal images can be obtained by the PTZ thermal imaging camera without any further processing. The machine condition monitoring system using the three-dimensional thermography may monitor all parts (including those of non-line-at-sight) of the machine with a minimum number of thermal imaging cameras. In addition, with the thermal images from different parts of the machine, three-dimensional thermal imaging can be produced so as to quickly and accurately locate any machine anomalies.

Figure 2:
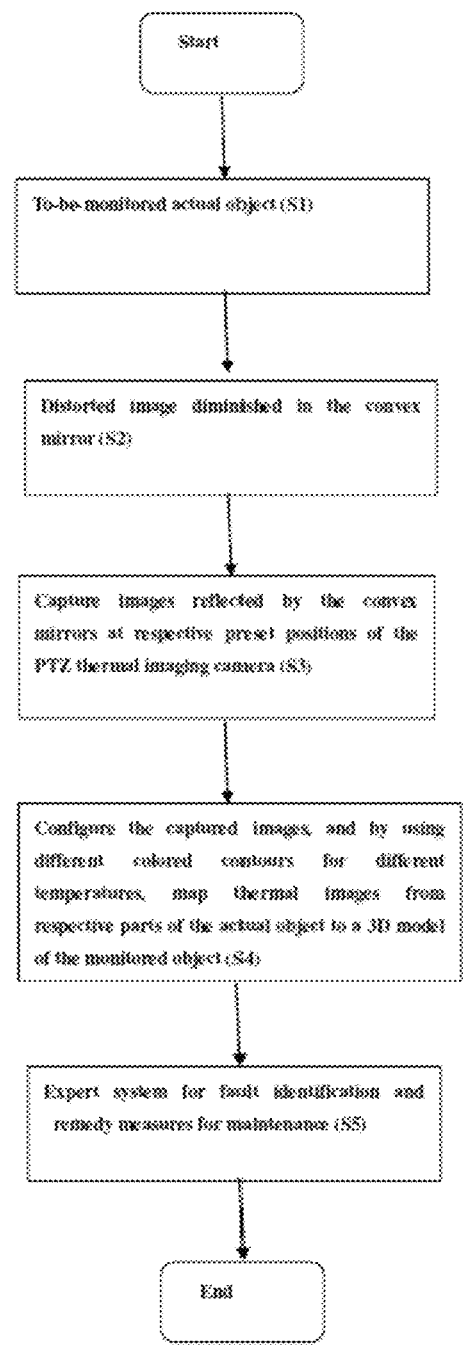
FIG. 2 is a work flow diagram of a machine condition monitoring system using three-dimensional thermography according to an embodiment of the present disclosure.

FIG. 2 is a work flow diagram of a machine condition monitoring system using three-dimensional thermography according to an embodiment of the present disclosure. As shown in FIG. 2, an actual object as a to-be-monitored object is determined first (step S1). Specifically, dependent on situations, one or more infrared reflective convex mirrors are installed at a plurality of strategical positions surrounding the monitored object so as to reflect infrared rays emitted from different parts of the object. Next, the infrared reflective convex mirrors will reflect the infrared rays emitted from different parts of the monitored object. Because the images reflected from the convex mirrors are smaller than the actual object, thermal images of more parts of the monitored object may also be obtained even in a narrow visual angle caused by the narrow environment in which the monitored object is located (step S2). Then, the reflected infrared rays from different convex mirrors are captured at different preset positions by a single PTZ thermal imaging camera. In other words, the PTZ thermal imaging camera may capture non-line-at-sight thermal images reflected from the convex mirrors and meanwhile directly obtain actual thermal images of the front of the line-at-sight monitored object (step S3). Next, the computer server needs to configure the thermal images reflected from the convex mirrors and captured by the PTZ thermal imaging camera, so as to obtain actual infrared energies from different parts of the monitored object. In addition, for the parts (e.g., line-at-sight parts) that can be directly monitored by the PTZ thermal imaging camera, the actual infrared energies of these parts may be directly obtained without the configuration processing. Then, by using different colored contours for different temperatures, the computer server maps the thermal images configured or directly obtained from different parts of the actual object to the three-dimensional model of the monitored object, thereby obtaining the three-dimensional thermal imaging of the monitored object (step S4). Finally, according to the obtained three-dimensional thermal imaging, predictive maintenance or the like is performed by further applying an expert system for fault identification and remedy measures for maintenance (step S5). For example, the computer server compares the temperatures of different parts of the monitored machine with the predefined threshold. If any unexpected hot spots or cold spots exist in the three-dimensional thermal image, an alert will be sent to the operator for notification. More preferably, change of the three-dimensional thermal imaging over time will also be recorded by the computer server, such that the operator may inspect an anomaly pattern over time so as to identify a fault type in the machine. What has been discussed above is the entire work flow diagram of the machine condition monitoring system according to an embodiment of the present disclosure.

It may be seen from the work flow diagram above that the present disclosure may locate thermal anomalies safely and precisely in a 3D model manner, which solves a technical problem in the prior art that it is very difficult to identify the positions of machine anomalies obtained in a 2D manner. In addition, different from the prior art which needs a plurality of thermal imagers to monitor the machine condition, the present disclosure may monitor all parts (including those non-line-at-sight parts) with a minimal number of thermal imaging cameras. Further, with the thermal images from different parts of the measured machine, 3D thermal imaging can be produced so as to quickly and precisely locate any machine anomalies; moreover, an alert will be automatically sent to the operator when any anomalies in the 3D thermal imaging of the machine are detected through an expert system or the like, which facilitates taking remedy measures on maintenance in advance, thereby implementing predicative maintenance.

Figure 3:
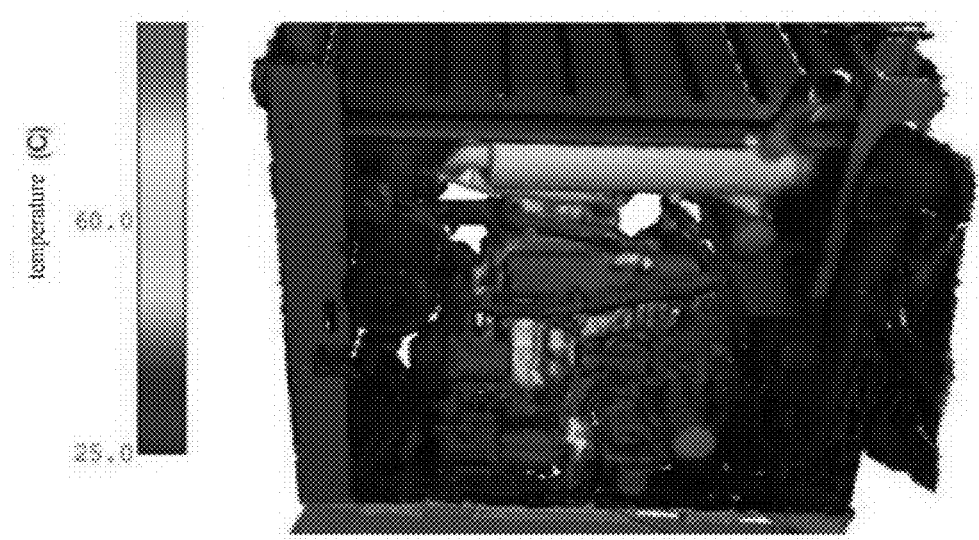
FIG. 3 is an instance of machine condition monitoring using three-dimensional thermography according to an embodiment of the present disclosure.
Figure 4:
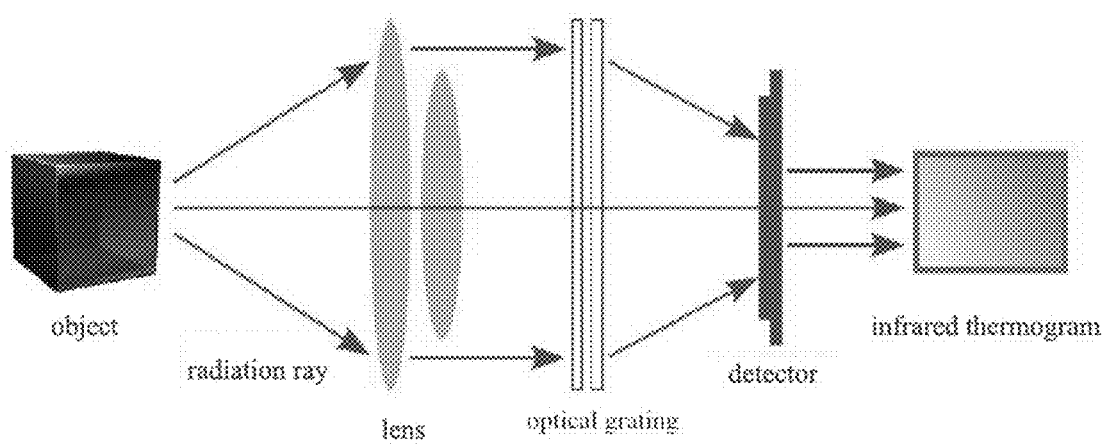
FIG. 4 is an optical path diagram of an infrared thermal imager as a prior art.

FIG. 3 is an instance of machine condition monitoring using three-dimensional thermography according to an embodiment of the present disclosure. As shown in FIG. 3, different colored regions on the three-dimensional thermal imaging of the to-be-monitored machine represent different temperatures of different parts of the monitored machine. By checking the three-dimensional thermal imaging, an operator of the machine condition monitoring system may clearly monitor working conditions of the machine (e.g., the power distribution transformer), and locate any thermal anomalies safely and precisely in a three-dimensional model manner. Further, the machine condition monitoring system using thermography may also automatically send an alert to the operator when detecting any anomalies in the 3D thermal imaging of the machine.

In view of the above, the technical solution of the present disclosure may be used to reduce investment on thermal inspection by light reflection and refraction and guarantee that the blocked non-line-at-sight parts may also be monitored through a minimal number of thermal imaging cameras. By using the 3D model, such as a building information model (BIM), thermal anomalies may be visualized and accurately located. The present disclosure enables monitoring of all parts of a machine (including non-line-at-sight parts) using a minimal number of thermal imaging cameras, without needing field human resources to monitor the machine. In addition, 3D thermal imaging can be produced using the thermal images from different parts of the machine, so as to quickly and accurately locate any anomalies of the machine. When any machine fault occurs, an alert will be automatically sent to the operator.

Those skilled in the art should understand that the exemplary embodiments may be implemented as computer readable codes on a computer readable recording medium. The computer readable recording medium refers to any data storage device that may store data and afterwards may be read by the computer system. Examples of the computer readable recording medium include: a read-only memory (ROM), a random access memory (RAM), a CD-ROM, a magnetic disk, a floppy disk, and an optical data storage device, etc. The computer readable recording mediums may also be distributed on networked computer systems, such that the computer readable codes are stored and executed in a distributed manner. Besides, the functional programs, codes, and code segments for implementing the exemplary embodiments may be easily interpreted by a person of normal skill in the art.

A person of normal skill in the art should be aware that what have been disclosed above are only preferred embodiments of the present disclosure. Of course, the scope of the rights of the present disclosure should not be limited thereto. Therefore, equivalent variations made according to the patented scope of the present disclosure still fall within the scope covered by the present disclosure. It should be understood that the depictions above are not intended for illustration, not for limitation. For example, the embodiments (and/or aspects thereof) may be used in combination with each other. In addition, various modifications may be made under the teaching of the present disclosure so as to adapt specific situations or materials without departing from the scope of the present disclosure.

What is claimed is:

1. A system for monitoring a working condition of a machine and recording three-dimensional thermal imaging of the machine, comprising: a pan-tilt-zoom thermal imaging camera (1), at least one infrared reflective convex mirror (2), and a computer server (3).

2. The system according to claim 1, characterized in that the infrared reflective convex mirrors (2) are installed at strategic positions surrounding the monitored machine so as to reflect infrared rays emitted from different parts of the machine, and the pan-tilt-zoom thermal imaging camera (1) captures reflected infrared rays from the convex mirrors (2) at different preset positions.

3. The system according to claim 1, characterized in that thermal images captured by the pan-tilt-zoom thermal imaging camera (1) are transmitted to the computer server (3) for image processing and recording.

4. The system according to claim 3, characterized in that the computer server (3) computes and configures the transmitted thermal images according to a plurality of physical characteristics so as to obtain actual infrared energies emitted from the machine.

5. The system according to claim 1, characterized in that the physical characteristics include a focal length of the convex mirror (2), a distance between the convex mirror (2) and the monitored machine, and a distance and angle between the pan-tilt-zoom thermal imaging camera (1) and the convex mirror (2).

6. The system according to claim 4, characterized in that the computer server (3) maps, by computing and configuring, thermal images from different parts of the monitored machine to a three-dimensional model of the machine, to obtain three-dimensional thermal imaging of the machine for further inspection.

7. The system according to claim 6, characterized in that the computer server (3) compares temperatures at different parts of the monitored machine with a predefined threshold and alerts an operator for notification if the three-dimensional thermal imaging has any unexpected hot spots or cold spots.

8. The system according to claim 7, characterized in that the computer server (3) records changes of the three-dimensional thermal imaging over time, such that an operator may inspect an anomaly pattern over time to identify a fault type in the monitored machine.

* * * * *